US00PP31770P3

(12) United States Plant Patent
de Boer

(10) Patent No.: US PP31,770 P3
(45) Date of Patent: May 19, 2020

(54) ***RUBUS* PLANT NAMED 'JDEBOER19'**

(50) Latin Name: *Rubus idaeus*
Varietal Denomination: JdeBoer19

(71) Applicant: Jan de Boer, Boelenslaan (NL)

(72) Inventor: Jan de Boer, Boelenslaan (NL)

( * ) Notice: Subject to any disclaimer, the term of this patent is extended or adjusted under 35 U.S.C. 154(b) by 0 days.

(21) Appl. No.: 16/501,073

(22) Filed: Feb. 19, 2019

(65) Prior Publication Data

US 2019/0269054 P1 Aug. 29, 2019

(30) Foreign Application Priority Data

Feb. 28, 2018 (QZ) ..... PBR 2018/0636

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 6/7499
See application file for complete search history.

*Primary Examiner* — Anne Marie Grunberg
(74) *Attorney, Agent, or Firm* — Penny J. Aguirre

(57) ABSTRACT

A new cultivar of *Rubus* plant named 'JdeBoer19' that is characterized by its fruit production on primocanes, its compact plant habit, its abundance of fruit with a sweet taste, and its canes with minimal thorns.

2 Drawing Sheets

Botanical classification: *Rubus idaeus.*
Cultivar designation: 'JdeBoer19'.

BACKGROUND OF THE INVENTION

The present invention relates to a new and distinct cultivar of *Rubus idaeus* named 'JdeBoer19' and will be referred to hereinafter by its cultivar name, 'JdeBoer19'. 'JdeBoer19' represents a new cultivar of raspberry plant grown for fruit production.

'JdeBoer19' was discovered by the Inventor as a chance seedling in 2010 in the Inventor's garden in Boelenslaan, The Netherlands. The parentage is unknown.

Asexual propagation of the new cultivar was first accomplished by the Inventor by stem cuttings in March of 2011 in Boelenslaan, The Netherlands. Asexual propagation of the new cultivar by stem cuttings has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'JdeBoer19' as a new and unique cultivar of *Rubus.*

1. 'JdeBoer19' exhibits fruit production on primocanes.
2. 'JdeBoer19' exhibits a compact plant habit.
3. 'JdeBoer19' exhibits an abundance of fruit with a sweet taste.
4. 'JdeBoer19' exhibits canes with minimal thorns.

'JdeBoer19' can also be to *Rubus* cultivars 'Nr7' (U.S. Plant Pat. No. 22,141), 'Boyne' (not patented) and 'Royalty' (not patented). 'Nr7' is similar to 'JdeBoer19' in having a compact plant habit. 'Nr7' differs from 'JdeBoer19' in producing fruit on floricanes. 'Boyne' is similar to 'JdeBoer19' in producing an abundance of sweet fruit on primocanes but differs from 'JdeBoer19' in having less compact plant habit. 'Royalty' is similar to 'JdeBoer19' in producing fruit on primocanes but differs from 'JdeBoer19' in having a less compact plant habit and in producing fruit that are purple-red in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1).

BRIEF DESCRIPTION OF THE DRAWINGS

The accompanying colored photographs illustrate the overall appearance and distinct characteristics of the new *Rubus*. The photographs were taken of a 3-years in age as grown outdoors in a trial garden in Boelenslaan, The Netherlands.

The photograph in FIG. 1 provides a side view of a plant of 'JdeBoer19'.

Figure 1:
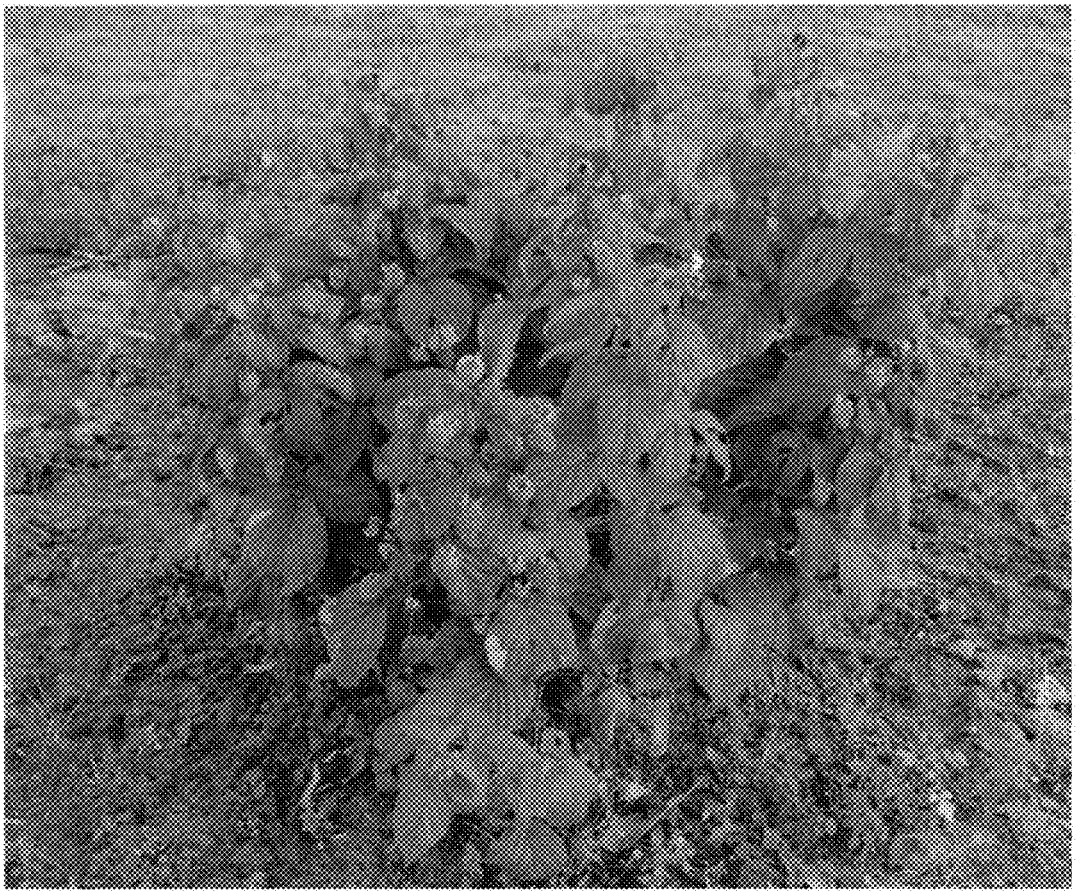
Figure 2:
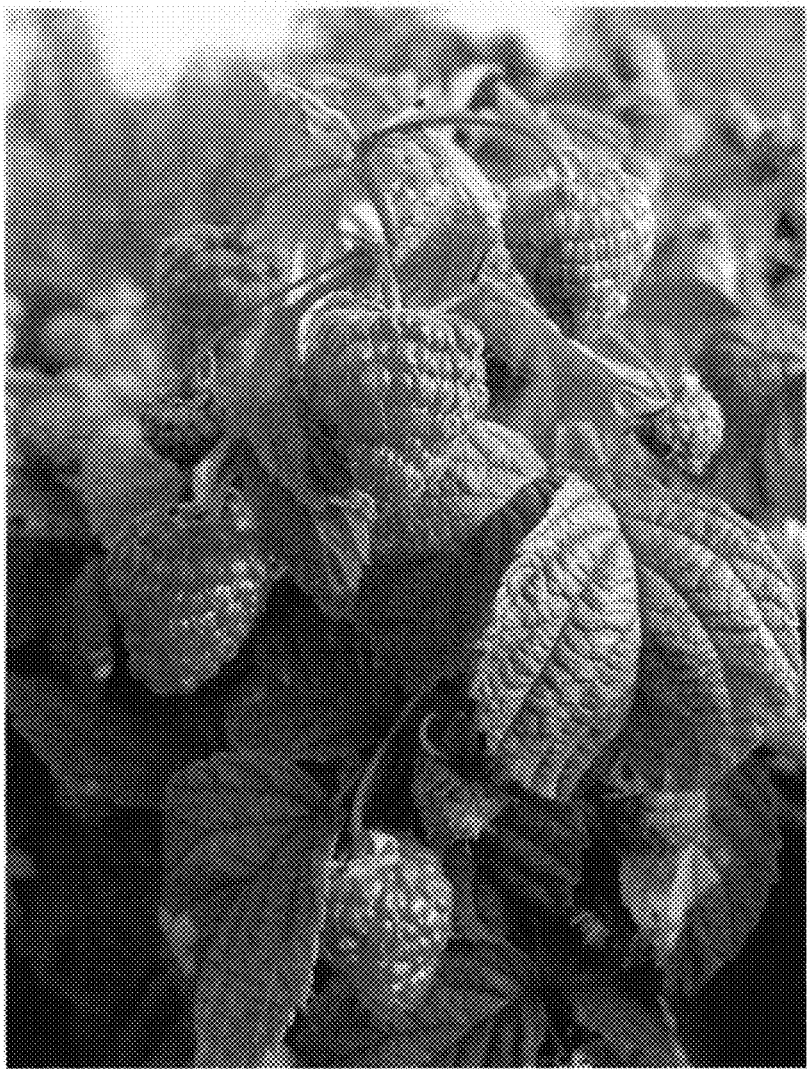

The photograph in FIG. 2 provides a close-up view of the fruit of 'JdeBoer19'.

The colors in the photographs are as close as possible with the photographic and printing technology utilized. The colors in the photograph may differ slightly from the color values cited in the detailed botanical description, which accurately describe the colors of the new *Rubus.*

DETAILED BOTANICAL DESCRIPTION OF THE PLANT

The following is a detailed description of plants 3-years in age as grown outdoors in a 5-liter container in Lottum, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Fruit producing perennial.

*Plant habit*.—Upright and compact.

*Height and spread*.—An average of 50 cm in height and 30 cm in diameter as a 3-year-old plant in a container.

*Cold hardiness*.—At least to U.S.D.A. Zone 5b.

*Diseases and pests*.—No resistance or susceptibility to pests or diseases has been observed.

*Root description*.—Fibrous, 165B in color with tips NN155D.

*Branching habit*.—Branching from the base, previous years growth either dies back in winter or is pruned.

*Propagation*.—Stem cuttings.

*Root development*.—An average of 6 to 8 weeks to initiate roots, an average of 4 months to fully develop roots as a young plant.

*Growth rate*.—Vigorous.

Cane description (primocanes):

*Cane size*.—An average of 40 to 60 cm in length and an average of 4 mm in diameter.

*Cane internode length*.—1 to 4 cm.

*Cane shape and aspect*.—Held at an average of 90° to soil levels with tips slightly bending.

*Cane strength*.—Strong, does not crack when bending.

*Cane color*.—The new canes N144D, mature canes 145C.

*Cane surface*.—Glabrous, minimal prickles; 1.2 mm to 1.2 cm in length and 0.3 mm in width, 187A in color.

Foliage description:

*Time of vegetative bud burst*.—March in The Netherlands.

*Leaf shape*.—Deltoid.

*Leaf arrangement*.—Alternate.

*Leaf division*.—Ternate.

*Leaf attachment*.—Petiolate.

*Leaf orientation*.—Outward to horizontal to downwards.

*Cross-sectional shape of terminal leaflet*.—Slightly concave to flat.

*Leaflet shape*.—Terminal; ovate, side; broadly lanceolate to elliptic.

*Leaflet quantity*.—An average of 10 per cane.

*Leaflet base*.—Terminal; rounded, side; rounded and slightly oblique.

*Leaflet apex*.—Acuminate.

*Leaflet fragrance*.—Light fragrance when crushed.

*Leaflet venation*.—Pinnate, 144B on upper surface and N144A on lower surface.

*Leaflet margins*.—Dentate.

*Leaflet position*.—Free (non touching).

*Leaflet substance*.—Thin.

*Leaflet attachment*.—Primarily sessile.

*Leaflet surface*.—Upper surface; glabrous, deeply recessed veins and just slightly reticulate, lower surface; raised veins and reticulate, covered with very short pubescence, upper surface 138D in color on young leaves and 157B in color on mature leaves.

*Leaflet color*.—Young leaf: upper surface 144A, lower surface 138C, mature leaf: upper surface NN137B, lower surface 138B.

*Leaflet size*.—Terminal; an average of 8 cm in length and 5 cm in width, side; average of 6 cm in length and 3 cm in width.

*Petioles*.—Round in shape, an average of 8 cm in length and 2 mm in width, color; upper surface 144B, lower surface 144C, strong, surface covered with very short pubescence, surfaces also covered with thorns an average of 2 to 7 per petiole; 0.5 to 0.7 mm in length, 187A in color, stipules; present at the base, average of 2, lanceolate to filiform in shape, 4 mm in length, 0.5 mm in width, average of 3 mm apart, 144B in color and quickly turning to 175A in color.

*Rachis*.—Round in shape, an average of 2 cm in length and 1.5 mm in width, color; upper surface 144B, lower surface 144C, surfaces sparsely pubescent, surfaces rarely covered with thorns with an average of 1, 0.1 mm in length and 187A in color.

Inflorescence description:

*Blooming period*.—As a primocane; mid-season; flowering for 8 weeks in summer in The Netherlands.

*Inflorescence*.—Open panicle, an average of 5 cm in length, an average of 8 cm in diameter.

*Rachis* (*peduncle*).—Glabrous surface, 1.3 mm in diameter, 5 cm in length, 144B in color.

*Pedicels*.—Round in shape, color 146D, an average of 4 cm in length and 9 mm in diameter, surface sparsely covered with very short pubescence, filiform in shape, prickles; 1 to 2, 0.5 mm in length and 187A in color, bracteoles; typically 2, 2 mm in length, 9 mm in width, lanceolate in shape.

*Flower buds*.—Triangular in shape, average of 6 mm in length and diameter, N144D and 146A in color, pubescent surface 157B in color.

*Flower type*.—Rotate, single, lastingness of a few days, not persistent.

*Flower number*.—1 to 12 per inflorescence.

*Flower fragrance*.—None.

*Flower size*.—Average of 1 cm in diameter and 8 mm in depth.

*Sepals*.—Five, persistent, an average of 9 mm in length and 5 mm in width, whorled, broadly ovate to lanceolate in shape, apex acute to acuminate, entire margin, inner surface color 144C, outer surface color 144B, 145D at apex, inner and outer surface sparsely covered with pubescence 157B in color.

*Petals*.—Five, persistent, whorled, an average of 5.5 mm in length and 2 mm in width, oblanceolate in shape, base cuneate, apex ranges between acute to obtuse to emarginate, entire margin, glabrous on upper and lower surfaces, color; when opening and fully open upper and lower surface NN155D.

*Receptacle*.—Ovate in shape, 3 mm in height, 2 mm in diameter, 138B in color.

*Androecium*.—An average of 60 stamens, filaments; 4 mm in length, glabrous surface, filiform and 157D in color, anthers; 0.5 mm in length, oblong in shape, color 157C, pollen; abundant in quantity and 156D in color.

*Gynoecium*.—An average of 80 pistils, filiform, 3 mm in length, 157D in color, stigmas; 145D in color, styles; 3 mm in length and 145D in color, ovary; 0.4 mm in length, 0.5 mm in width, 142B in color with pubescence 157D in color.

*Fertility*.—Self-fertile.

Fruit description:

*Fruit number*.—An average of 20 per cane.

*Fruit size*.—An average of 1.8 cm in length and 1.6 cm in diameter.

*Fruit shape*.—Broadly ovate.

*Fruit form*.—Aggregate fruit.

*Fruit hanging angle*.—Nodding.

*Fruit druplets*.—Up to 80 per fruit, firm texture, obovate in shape, 5 mm in length, 4 mm in diameter, 46A in color, surface covered with short pubescent hairs, stigma and style present.

*Fruit attachment*.—Quickly falling when ripe.

*Fruit weight*.—3 to 4 g/fruit.

*Fruit receptacle*.—Persistent, ovate in shape, 1 cm in length, 8 mm in diameter, 11C in color.

*Fruit maturity date*.—July to October in The Netherlands.

*Seed*.—Cymbiform in shape, 1 per druplet, 3 mm in length, 1.2 mm in diameter, 163A in color.

*Cropping frequency*.—Annually, on primocanes.

*Flavor*.—Sweet.

*Brix*.—5°.

*Shelf life*.—An average of 7 days after picking.

*Market use*.—Fresh fruit.

It is claimed:

1. A new and distinct cultivar of *Rubus* plant named 'JdeBoer19' as herein illustrated and described.

* * * * *